United States Patent [19]

Miao et al.

[11] Patent Number: 5,030,647

[45] Date of Patent: Jul. 9, 1991

[54] ANTI-INFLAMMATORY THIENYLBENZYLAMINE COMPOUNDS

[75] Inventors: Clara K. Miao, Trumbull; Karl G. Grozinger, Ridgefield; Robert Rothlein, Danbury, all of Conn.; Ronald Faanes, Pound Ridge, N.Y.; Genus Possanza, Ridgefield; John P. Devlin, Sharon, both of Conn.

[73] Assignee: Boehringer Ingelheim Pharmaceuticals, Inc., Ridgefield, Conn.

[21] Appl. No.: 478,104

[22] Filed: Feb. 9, 1990

[51] Int. Cl.$^5$ .................. A61K 31/38; C07D 333/22
[52] U.S. Cl. .................. 514/414; 514/438; 514/448; 549/70; 549/72; 549/74; 549/75; 549/77; 548/466
[58] Field of Search ............. 548/466; 549/70, 72, 549/74, 75, 77; 514/438, 448, 414

[56] References Cited

U.S. PATENT DOCUMENTS 4,198,519  4/1980  Goudie ........................ 549/70
4,927,835  5/1990  Kise et al. .................... 514/448

FOREIGN PATENT DOCUMENTS 137201  4/1984  Japan .

Primary Examiner—Mukund J. Shah
Assistant Examiner—Matthew V. Grumbling

Attorney, Agent, or Firm—Daniel Reitenbach; Mary-Ellen M. Timbers; David E. Frankhouser

[57] ABSTRACT

Novel thienylbenzylamine compounds of the formula

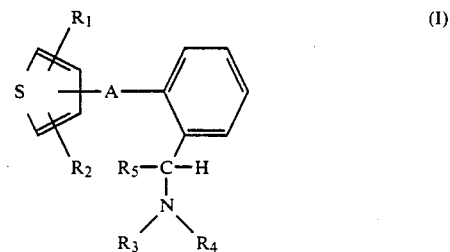

(I)

or

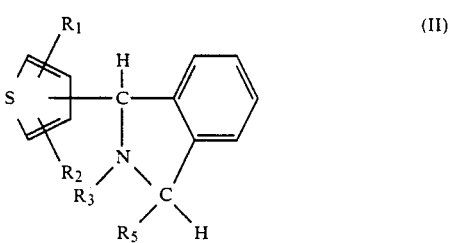

(II)

wherein A and $R_1$–$R_5$ are defined herein. These compounds are useful for the treatment of inflammation.

21 Claims, No Drawings

ANTI-INFLAMMATORY THIENYLBENZYLAMINE COMPOUNDS

FIELD OF THE INVENTION

This invention is related to novel thienylbenzylamine compounds, methods for their use in the treatment of inflammation and compositions comprising the novel thienylbenzylamine compounds.

BACKGROUND

Certain benzylamines are known in the art. U.S. Pat. No. 3,635,974 describes α-phenyl-2-aminomethyl-benzylalcohols useful as anorectics in warm-blooded animals. U.S. Pat. No. 3,728,460 describes anorectic pharmaceutical compositions containing certain 2-(methylaminomethyl)-α-(4'-halo-phenyl)-benzyl alcohols as active ingredients. In Freter et al, "A New Group of Anorexingenic Compounds" J. Med. Chem 13, 1228 (1970), there is described the structure and anoxerigenic activity of a group of substituted aminomethylbenzhydrols. Benzylamine compounds are also described in British Patent No. 984,363; French Patent No. 1,549,342; Netherlands Patent No. 6,606,390; German Offenlegungeschrift 2834312; Freter et al, "2-Aminomethyl-benzhydrols", Can. J. Chem 48 (11), 1670 (1970); and Freter et al, "A New Tetrahydroisoquinoline Synthesis", J. Het. Chem 7, 159 (1970).

It is the purpose of this invention to provide a novel class of thienylbenzylamine compounds. It is also the purpose of this invention to provide a method of using the novel thienylbenzylamine compounds in the treatment of inflammation.

DESCRIPTION OF THE INVENTION

This invention relates to a novel class of compounds represented by the formula:

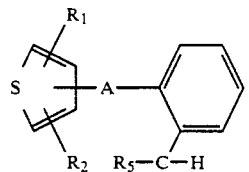

(I)

or

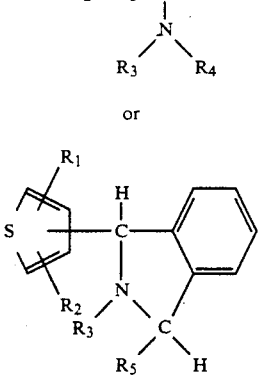

(II)

wherein $R_1$ is hydrogen, phenyl, halogen, alkyl of from 1 to 5 carbon atoms, dialkylaminoalkyl of from 3 to 5 carbon atoms, or acyl of from 3 to 5 carbon atoms;

$R_2$ is hydrogen, halogen or alkyl of from 1 to 5 carbon atoms; $R_3$ and $R_4$ are each hydrogen, alkyl of from 1 to 5 carbon atoms, or hydroxyalkyl of from 1 to 2 carbon atoms; $R_5$ is hydrogen or alkyl of from 1 to 5 carbon atoms; and

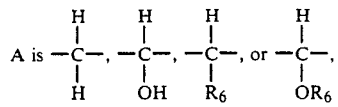

wherein $R_6$ is alkyl of from 1 to 5 carbon atoms, or physiologically acceptable salts thereof.

Preferably $R_1$ is hydrogen, halogen or methyl;
$R_2$ is hydrogen, halogen or methyl;
$R_3$ is hydrogen or methyl;
$R_4$ is hydrogen or methyl;
$R_5$ is hydrogen or methyl; and

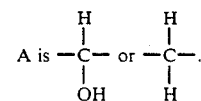

Most preferably, $R_1$ is halogen;
$R_2$ is halogen;
$R_3$ is methyl;
$R_4$ is methyl;
$R_5$ is hydrogen or methyl; and

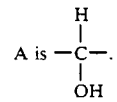

For the purpose of this invention, "inflammation" means any physiological process which involves the recruitment and/or activation of leucocytes. Examples of inflammation treatable in accordance with the present invention include, for example, inflammation associated with skin infections, autoimmune states, granulomatos diseases, tuberculosis, sarcoidosis and Crohne's Disease.

Compounds of this invention can be prepared by the process illustrated below.

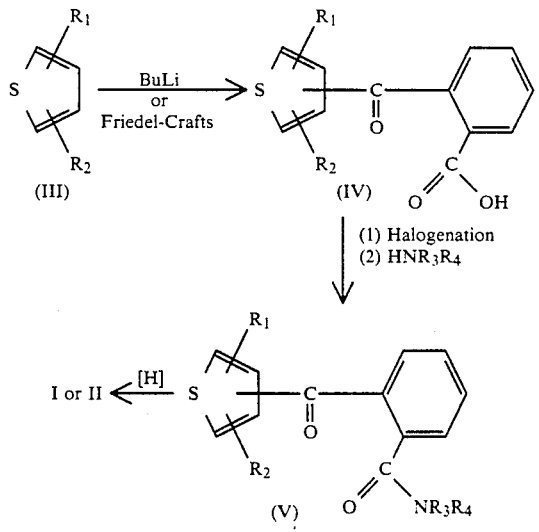

A substituted thiophene compound (III) is dissolved in an inert solvent such as tetrahydrofuran at a low temperature in the presence of a proton abstractor such as n-butyllithium to produce an anion of the substituted thiophene compound. The anion of the substituted thiophene compound is then reacted with phthalic anhydride at temperatures which can vary from 10° C. to refluxing temperatures, to produce Compound IV. Compound IV can also be produced by Friedel-Crafts acylation of the substituted thiophene (III) with phthalic anhydride in an inert solvent such as a dichloroethane under reflux conditions (See, e.g. Badger et al, J. Chem. Soc. (1954), 4162). Compound IV is then reacted with a thionyl chloride or other halogenating agent to produce an acid halide of Compound IV. The acid halide is then reacted with an alkylamine or other appropriate amine to produce Compound V. Compound V is then reduced to produce a compound of Formula I or II.

The compounds of this invention can also be prepared by the alternate process illustrated below.

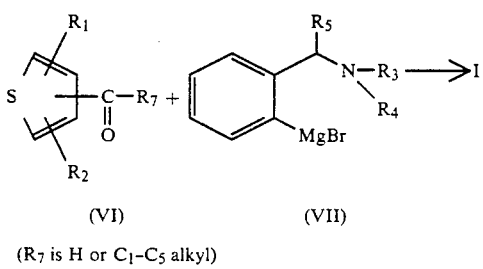

(VI)  (VII)

($R_7$ is H or $C_1$-$C_5$ alkyl)

A substituted thiophene compound (VI) is reacted with a Grignard reagent (VII) in dried ether at room temperature to produce a compound of Formula I.

This invention also relates to method for treating inflammation in a patient requiring such treatment, which comprises administering to the patient a therapeutically effective amount of a compound of the formula

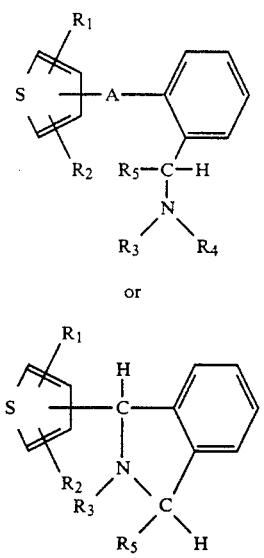

wherein A and $R_1$-$R_5$ are as defined above.

The compounds of this invention can be administered to treat inflammation by any means or route of administration that produces contact of the compound with its site of action in the body of the individual human or animal under treatment. The compound can be administered by known conventional routes of administration such as by oral administration, or injection. The compound is usually administered in dosage forms which deliver it in a conventional pharmaceutical carrier or mixtures thereof which are selected on the basis of the particular route of administration and rate of delivery to the site of action which is desired.

Dosage forms (compositions) which are suitable for internal administration of the compounds include oral administration forms such as tablets, coated tablets, capsules, syrups, elixirs or suspensions. Such carriers for each applicable route of administration are described in Remington's Pharmaceutical Sciences.

The range of dosages in which the compound in accordance with the invention can be administered will vary depending upon the route of administration selected as well as the characteristics of the intended recipient, including age, body weight, general state of health and the like. Usually, the compound of the invention is administered in unit doses of from about 1 to about 100 mgs and from about 1 to about 4 times daily. Such unit doses can be combined in metered release dosage forms for sustained single dose release of the compound.

EXAMPLE 1

A. Preparation of
o-(5-Chloro-2-thiophene)carbonyl-benzoic acid

I. FRIEDEL-CRAFTS ACYLATION

To 500 ml of 1,2-dichloroethane was added 24.2 g (0.2 moles) of 2-chlorothiophene and 20 g (0.135 mole) of phthalic anhydride, to produce a starting solution. To the starting solution was added 35.98 g (0.27 mole) of $AlCl_3$. The resulting mixture was refluxed for 3 hr. The mixture was then cooled to 0° C. in ice/$H_2O$. Water was then added to the mixture to decompose excess $AlCl_3$, producing an aqueous phase and an organic phase. The aqueous phase of the mixture was acidified to pH 1 through the addition of 2N HCl. The mixture was then filtered through celite to remove the inorganic precipitate before separation of the organic and aqueous phases was conducted. The organic phase was dried over anhydrous. $MgSO_4$, filtered and concentrated to give a dark oily material. This oily material was purified through a silica gel column packed in $CH_2Cl_2$. The o-(5-chloro-2-thiophene)carbonyl-benzoic acid was eluted at 3% MeOH in $CH_2Cl_2$ in the form of a dark oil (36.5 g). The oil was then treated with neutral charcoal and filtered through Celite, concentrated and crystallized from $CH_2Cl_2$/pettroleum-ether (pet-ether) to provide 29.3 g (55%) white crystalline product, mp 124°–125° C.

Elemental Analysis: $C_{12}H_7ClO_3S$.

Calculated: C, 54.05; H, 2.65; Cl, 13.29; S, 12.02.

Found C, 54.12; H, 2.72; Cl, 13.51; S, 12.23.

II. ANIONIC METHOD To 100 ml of freshly distilled tetrahydrofuran (THF) was added 5.0 g (42.2 mmoles) of 2 chlorothiophene at −78° C., to produce a starting solution. To the starting solution was added 16.9 mL (42.2 mmoles) of a 2.5M solution of BuLi. The resulting mixture was kept at between −60° C. to −65° C. An orange anionic solution was generated. After stirring for 1½ hrs. at −78° C., the mixture was added dropwise through a cannula needle to a solution of 6.25 g (42.2 mmoles) of phthalic anhydride in 125 mL dry THF at −10° C. to form a reaction mixture. The reaction mixture was stirred for an additional 5½ hr. at −10° C. before it was quenched with $H_2O$ and acidified with 2N HCl, producing an aqueous phase and an organic phase. The aqueous phase was extracted with ether (2 x). The combined ether extracts were washed once with $H_2O$, dried over $MgSO_4$, filtered and concentrated to give 12.1 g oil. Following the same purification method as in A provided 7.7 g (68%) of crystalline product.

B. Preparation of o-(5-chloro-2-thiophene)carbonyl dimethyl amide 16.7 g (14.0 mmole,) of thionyl chloride was added to a solution of 7.5 g (2.7 mmole) of the product prepared in A (I) in 75 mL $CH_2Cl_2$. The resulting mixture was refluxed for 2 hr. The mixture was then concentrated on a rotary evaporator. The resulting oil was re-dissolved into 100 mL $CH_2Cl_2$ and the resulting solution was cooled in an ice bath. Gaseous dimethylamine was bubbled into the solution for 10 min. at which point $H_2O$ was added and the aqueous and organic phases were separated. The aqueous phase was further extracted with $CH_2Cl_2$(2 x). The combined extracts were dried over anhydrous. $Na_2SO_4$, filtered and concentrated to give 10.8 g residue which was filtered through silica gel using 5% EtOH in $CH_2Cl_2$ to give 7.95 g of a yellow oil. Flash column chromatography eluting with 2% acetone in $CH_2Cl_2$ gave 6.6 g (80%) of o-(5-chloro-2-thiophene)carbonyldimethylamide in the form of a viscous oil.

C. Preparation of 5-chloro-2[(2-dimethylaminomethylphenyl)hydroxymethyl]thiophene To 3.8 g (12.9 mmole) of the O-(5-chloro-2-thiophene)carbony)dimethylamide prepared in B in 40 mL of freshly distilled THF was added under $N_2$ 26 mL (26 mmole) of 1.0 M lithium aluminum hydride (LAH) in THF with stirring at room temperature. The resulting mixture was refluxed for 1 hr. After cooling to room temperature, 2 mL $H_2O$ was then added slowly to the mixture. This was then followed by the addition of anhydrous $Na_2SO_4$. The resultant mixture was filtered to remove the inorganic salt and the filtrate was saved. The filtered cake residue of inorganic salt was then washed well with ether and the ether filtrate was combined with the first filtrate. The combined filtrate solution was then concentrated to give 3.3g oily material. Flash column chromatography of the material on Silica Gel and eluted with 2% Acetone in Pet-Ether provided 2.2 g (61%) of the pure crystalline product (mp 77.5°-78.5°) after recrystallizing from ether/pet-ether.
Elemental Analysis: $C_{14}H_{16}ClNOS$
Calculated: C, 59.67; H, 5.72; Cl, 12.58; N, 4.97; S, 11.38
Found: C, 59.62; H, 5.98; Cl, 12.39; N, 4.92; S, 11.37

D. Hydrochloride salt of 5-chloro-2[(2-dimethylaminomethylphenyl) hydroxymethyl]thiophene 1.0 g of the 5-chloro-2-[(2-dimethylaminomethylphenyl)hydroxymethyl]thiophene prepared in C was dissolved in ether. The etheral solution was cooled to −80° C. Upon addition of an ethereal HCl solution a white precipitate was obtained which was immediately filtered under $N_2$ and dried in high vacuum without heating. The resultant hydrochloride salt was extremely hygroscopic and unstable in air.

Elemental Analysis: $C_{14}H_{17}Cl_2NOS$.
Calculated: C, 52.83; H, 5.38; Cl, 22.28; N, 4.40; S, 10.08
Found: C, 52.80; H, 5.34; Cl, 21.99; N. 4.21; S, 9.98

EXAMPLE 2

Preparation of 5-chloro-2-[(2-dimethylaminomethylphenyl) ethoxymethyl]thiophene

To a solution of 820 mg (2.95 mmole) 5-chloro-2[(2-dimethylaminomethylpheny)hydroxymethyl] thiophene in 50 mL reagent alcohol was bubbled gaseous HCl until the solution was acidic. The solution was then allowed to stand overnight at room temperature. After the removal of the alcohol from the solution on a rotary evaporator, aqueous $NaHCO_3$ was added to the residue, which produced an aqueous phase and an organic phase. The aqueous phase was extracted 3 x with $CH_2Cl_2$. The combined $CH_2Cl_2$ extracts were dried over anhydrous $MgSO_4$, filtered and concentrated to give 900 mg of oily material. Flash column chromatography with sil gel by eluting initially with pet-ether followed by 2% acetone in pet-ether. 700 mg of 5-chloro-2[(2-dimethylaminomethylphenyl)ethoxymethyl]thiophene in the form of clear oil was obtained.

| Elemental Analysis: $C_{16}H_2ONOSCl$ | | | | |
| --- | --- | --- | --- | --- |
| C | H | N | S | Cl |
| Calc.: 62.02 | 6.51 | 4.52 | 10.35 | 11.44 |
| Found: 62.23 | 6.51 | 4.32 | 10.30 | 11.64 |

EXAMPLE 3

Preparation of 5-chloro-2-(2-dimethylaminomethylphenylmethyl) thiophene

To a solution of 12.05 g (0.041 mole) of O-(5-chloro-2-thiophene) carbonyl dimethyl amide in 100 mL THF was syringed 123 mL of 1M solution of $BH_3THF$ in THF, under argon. The resulting mixture was refluxed for 4 hrs. The mixture was then cooled and 10 mL of a 6N HCl solution was added slowly; a vigorous gas solution was observed initially. The resulting acidic mixture was refluxed for ½ hr. 35 mL of a 2N NaOH solution was then added and the resultant mixture was extracted 2x with $CH_2Cl_2$. The combined $CH_2Cl_2$ extracts were dried over anhydrous $Na_2SO_4$, filtered and concentrated to give 12 g of oil. Flash column chromatography 3x starting with pet-ether followed by increments of acetone 2%, 3%, 5%. 3.47 g (32% yield) of 5-chloro-2-(2-dimethylaminomethylphenylmethyl)thiophene was obtained in the form of oil.

| Elemental Analysis $C_{14}H_{16}NSCl$ | | | | | |
|---|---|---|---|---|---|
| | C | H | N | S | Cl |
| Calc. | 63.26 | 6.07 | 5.27 | 12.06 | 13.34 |
| Found | 63.44 | 6.11 | 5.12 | 12.21 | 13.15 |

EXAMPLE 4

Preparation of 3-(2-dimethylaminomethylphenyl)hydroxymethyl]thiophene

A. Preparation of Grignard reagent (magnesium complex of 2-bromo-N,N-dimethyl-benzylamine)

To a one liter 3 necked round bottom flask equipped with a condenser, calcium chloride tube, a by-pass dropping funnel, and a nitrogen inlet tube, was added 2.32 g of magnesium and a crystal of iodine. This dry mixture was then heated with a heat gun until all the iodine was sublimed. 2-bromo-N,N-dimethyl benzylamine (23 g, 0.107 mol) was added at approx. 60° C. followed by the slow addition of 400 ml of sodium dried ether. The resultant mixture was heated vigorously under reflux. Within two hours, most of the magnesium had reacted producing a cloudy solution comprising the magnesium complex of 2-bromo-N,N-dimethyl-benzylamine. The cloudy solution was siphoned out under nitrogen to a bypass funnel having a glass wool plug to filter the solution. The filtrate contained the Grignard reagent and was stored at 4° C. for several days.

B. Preparation of Grignard reagent (magnesium complex of 2-bromo [1-(N,N-dimethylamino) ethyl] benzene)

The same procedure as described in A was used except that 2-bromo[1-(N,N-dimethylamino)ethyl]benzene was used in place of 2-bromo-N,N-dimethylbenzylamine.

C. Preparation of 3-(2-dimethylaminomethylphenyl)hydroxymethyl]thiophene

The Grignard reagent prepared in A was added dropwise to a stirred solution of 3-thiophene carboxyaldehyde (11.2 g 0.1 mol) in 300 ml of dried ether. The mixture was stirred at room temperature overnight, then poured into water, and then acidified with ammonium chloride producing an aqueous phase and an ether phase. The ether phase was separated, dried over sodium sulfate and concentrated. The crude product was purified by chromatography using silica gel. Recrystallization from ether/petroleum ether gave 30.0 g (80.9%) (mp 77°–78° C.) of 3-[(2-dimethylaminomethylphenyl)hydroxymethyl]thiophene.

Anal. calc. for $C_{14}H_{17}NOS$
C, 67.98; H, 6.93; N, 5.66; S 12.96
Found C, 68.09; H, 6.86; N, 5.60; S 12.75.

EXAMPLE 5

Preparation of N,N-dimethyl-2-[1-(5-chlorothien-2-yl)-1-hydroxyethyl]benzylamine The same procedure as described in Example 4C was used except that 4-chloro-2-acetyl thiophene was substituted for the 3-thiophene carboxyaldehyde.

EXAMPLE 6

Preparation of 3-(2-N,N-dimethylaminomethylphenyl)carbonyl]thiophene

A solution of chromium trioxide (4 g) in sulfuric acid (3 ml) and water (30 ml) was added dropwise to a stirred solution of the compound prepared in Example 1C (12 g) in 250 ml of acetone. The resultant mixture was stirred for three hours, the acetone was evaporated, the residue neutralized with sodium carbonate. The product was extracted into methylene chloride, dried and purified by column chromatography to give 9.3 g (mp 59°–60° C.) of 3-[(2-N,N-dimethylaminomethylphenyl)carbonyl]thiophene.

Analysis Cal. for $C_{14}H_{15}NOS$
C, 68.54; H, 6.16; N, 5.70; S 13.07%.
Found C, 68.75; H, 6.27, N, 5.64; S 13.05%.

EXAMPLE 7

For the purposes of this example and Example 8 below, the compounds shall be referred to by their respective numbers as designated below:

| COMPOUND NUMBER | COMPOUND NAME |
|---|---|
| 1. | 5-chloro-2-[(2-dimethylaminomethylphenyl) hydroxymethyl]thiophene |
| 2. | 5-chloro-2-[(2-dimethylaminomethylphenyl) hydroxymethyl]thiophene hydrochloride |
| 3. | 2-[(2-Dimethylaminomethylphenyl)hydroxymethyl] thiophene |
| 4. | 2-[(2-dimethylaminomethylphenyl)hydroxymethyl]-5-methyl-thiophene |
| 5. | 3-chloro-2-[(2-dimethylaminomethylphenyl) hydroxymethyl]thiophene |
| 6. | 5-chloro-2-[(2-diethylaminomethylphenyl) hydroxymethyl]thiophene |
| 7. | 5-chloro-2-[(2-dimethylaminomethylphenyl) ethoxymethyl]thiophene |
| 8. | 5-chloro-2-[(2-(N,N-methylethanolaminomethylphenyl)hydroxymethyl]thiophene |
| 9. | 5-chloro-2-[2-(N,N-diethanolaminomethylphenyl)methoxy methyl]thiophene |
| 10. | 5-N,N-dimethylaminomethyl-2-[2-(N,N-dimethylaminomethylphenyl)hydroxymethyl] thiophene |
| 11. | 5-chloro-2-(2-dimethylaminomethyl benzoyl) thiophene |
| 12. | 5-chloro-2-(2-dimethylaminomethylphenylmethyl)thiophene |
| 13. | 5-chloro-2-[(dimethylaminomethylphenyl)hydroxymethyl]-3-methylthiophene |
| 14. | 2-[1-(N-methylisoindolinyl]-5-chlorothiophene |
| 15. | 5-bromo-2-[(2-dimethylaminomethylphenyl hydroxymethyl]thiophene |
| 16. | 5-chloro-2-[-(2-dimethylaminomethylphenyl)-1-hydroxymethyl]thiophene monofumarate |
| 17. | 3-bromo-2-[(2-dimethylaminomethylphenyl)hydroxymethyl]thiophene monofumarate |
| 18. | 4-bromo-2-[(2-dimethylaminomethylphenyl)hydroxymethyl] thiophene |
| 19. | 2-[(2-dimethylaminomethylphenyl)hydroxymethyl]-5-(1,1-ethylenedioxyethyl) thiophene |
| 20. | 5-acetyl-2-[(2-dimethylaminomethylphenyl) hydroxymethyl]thiophene |
| 21. | 3-[(2-dimethylaminomethylphenyl)hydroxymethyl thiophene |
| 22. | 2-chloro-3-[(2-N,N-dimethylaminomethylphenyl)hydroxymethyl]thiophene hydrochloride |

-continued

| COMPOUND NUMBER | COMPOUND NAME |
|---|---|
| 23. | 5-bromo-3-[(2-N,N-dimethylaminomethylphenyl)hydroxymethyl] thiophene hydrochloride |
| 24. | 5-chloro-3-[(2-N,N-dimethylaminomethylphenyl)hydroxymethyl]thiophene hydrochloride |
| 25. | 2,5-dichloro-3[(2-N,N-dimethylaminomethylphenyl)hydroxymethyl]thiophene hydrochloride |
| 26. | 4-bromo-3-[(2-N,N-dimethylaminomethylphenyl)hydroxymethyl]thiophene hydrochloride |
| 27. | 3,4-dibromo-2-[(2-N,N-dimethylaminomethylphenyl)hydroxymethyl]thiophene hydrochloride |
| 28. | 5-iodo-3-[(2-N,N-dimethylaminomethylphenyl)hydroxymethyl]thiophene hydrochloride |
| 29. | 2,5-diiodo-3-[(2-N,N-dimethylaminomethylphenyl)hydroxymethyl]thiophene hydrochloride |
| 30. | 4,5-dichloro-3-[(2-N,N-dimethylaminomethylphenyl)hydroxymethyl]thiophene hydrochloride |
| 31. | 2,4,5-Trichloro-3-[(2-N,N-dimethylaminomethylphenyl)hydroxymethyl]thiophene hydrochloride |
| 32. | 3,5-dichloro-2-[(N,N-dimethylaminomethylphenyl)hydroxymethyl]thiophene hydrochloride |
| 33. | N,N-dimethyl-2-[1-(5-chlorothien-2-yl)-1-hydroxyethyl]benzylamine hydrochloride |
| 34. | N,N-dimethyl-2-[1-(5-bromothien-2-yl)-1-hydroxyethyl]benzylamine |
| 35. | 5-bromo-3-[2-(1-N,N-dimethylaminoethylphenyl)hydroxymethyl]thiophene |
| 36. | 5-chloro-2-[2-(1-N,N-dimethylaminoethylphenyl)hydroxymethyl]thiophene hydrochloride |
| 37. | 3-[2-(2-N,N-dimethylaminomethylphenyl)carbonyl]thiophene |
| 38. | 5-bromo-3-[2-(1-N,N-dimethylaminoethylphenyl)carbonyl]thiophene hydrochloride |

REVERSE PASSIVE ARTHUS REACTION

The reverse passive Arthus reaction is initiated by the interaction of antigen and antibody resulting in the formation of a precipitating immune complex, followed by fixation of complement, accumulation of leukocytes, edema and hemorrhage. The immunopathology of rheumatoid arthritis involves many of the parameters found in this reaction.

Test groups (5 rats per group) are dosed orally with compounds one hour prior to the sub-plantar injection into the right hind paw of rabbit anti-ovalbumin antibody (50 μg/0.1 ml). Immediately afterwards, ovalbumin (Sigma, #5503) (5 mg/0.2 ml) is injected i.v. via the tail vein. The right hind paw volume is measured at hourly intervals, from one to four hours after the injection of the immune reactants.

The change in paw volume for each animal is calculated by subtracting zero hour paw volume (before injection) from the paw volume at the time of measurement. The mean of these values is calculated for each group. Results are expressed in Table I below as percent inhibition of paw swelling compared to untreated controls.

TABLE I

| COMPOUND | DOSAGE (mg/kg) | % INHIBITION HOUR | | |
|---|---|---|---|---|
| | | 2 | 3 | 4 |
| 1 | 100 | 87.5 | 71.5 | 67.8 |
| | 100 | 74.1 | 88.9 | 81.0 |

TABLE I-continued

| COMPOUND | DOSAGE (mg/kg) | % INHIBITION HOUR | | |
|---|---|---|---|---|
| | | 2 | 3 | 4 |
| | 30 | 61.3 | 57.8 | 19.7 |
| | 30 | 58.8 | 44.6 | 32.4 |
| | 10 | 54.0 | 23.1 | 17.1 |
| 3 | 30 | 43.3 | 22.8 | 0 |
| 4 | 30 | 43.1 | 19.8 | 4.2 |
| 5 | 30 | 35.6 | 13.6 | 32.3 |
| 6 | 30 | 46.0 | 35.9 | 0.0 |
| 7 | 30 | 24.2 | 0.0 | 0.0 |
| 8 | 30 | 26.9 | 18.2 | 2.8 |
| 9 | 30 | 20.8 | 3.6 | 0.0 |
| 10 | 30 | 55.6 | 21.6 | 19.4 |
| 11 | 30 | 40.5 | 18.8 | 1.5 |
| 12 | 30 | 65.8 | 51.1 | 25.5 |
| 13 | 30 | 66.8 | 24.1 | 7.3 |
| | 100 | 51.7 | 28.6 | 3.3 |
| 14 | 30 | 64.4 | 49.9 | 17.8 |
| 15 | 30 | 63.1 | 47.1 | 26.7 |
| 16 | 30 | 17 | 11 | 0 |
| 17 | 30 | 49 | 5 | 0 |
| 18 | 30 | 35 | 37 | 40 |
| 19 | 30 | 40 | 37 | 11 |
| 20 | 30 | 12 | 15 | 2 |
| 21 | 30 | 39 | 18 | 30 |
| 22 | 30 | 22 | 0 | 0 |
| 23 | 30 | 72 | 66 | 44 |
| 24 | 30 | 51 | 54 | 53 |
| 25 | 30 | 68 | 64 | 38 |
| 26 | 30 | 42 | 25 | 6 |
| 27 | 30 | 39 | 25 | 10 |
| 28 | 30 | 21 | 0 | 13 |
| 29 | 30 | 50 | 29 | 0 |
| 30 | 30 | 47 | 36 | — |
| 31 | 30 | 44 | 32 | 0 |
| 32 | 30 | 62 | 47 | 12 |
| 33 | 30 | 66 | 60 | 40 |
| 34 | 30 | 66 | 49 | 14 |
| 35 | 30 | 58 | 48 | 9 |
| 36 | 30 | 52 | 15 | 3 |
| 37 | 30 | 0 | 0 | 0 |

EXAMPLE 8

CHEMOTAXIS OF HUMAN PERIPHERAL LEUKOCYTES

A) Red blood cell lysing solution

Dissolved: 8.0 gm ammonium chloride (0.15 M $NH_4Cl$)
1.0 gm potassium bicarbonate (0.01 M $KHCO_3$) and
0.3 gm EDTA (0.001 M) in 1000 ml $H_2O$
Adjusted to pH 7.2 prior to use.

B) Stock salt solution

Dissolved:
80 gm of sodium chloride (NaCl)
4 gm of potassium chloride (KCl)
1 gm of sodium phosphate dibasic ($Na_2HPO_4$)
1 gm of potassium phosphate ($KH_2PO_4$) in 1000 ml $H_2O$ C) Solution for Hanks Buffer
1) Dissolved 121.1 gm Tris Base (1M) in 1000 ml $H_2O$; adjust pH to 7.3.
2) Dissolved 11.1 gm calcium chloride ($CaCl_2$; 0.1M) in 100 ml $H_2O$.
3) Dissolved 2.4 gm magnesium sulfate ($MgSO_4$; 0.4M) in 100 ml $H_2O$.
4) Dissolved 14 gm sodium bicarbonate ($NaHC_3$) in 1000 ml $H_2O$.

D) Hanks Balance Salt Solution (HBSS)

| | |
|---|---|
| Stock salt solution | 10 ml |
| Tris | 2.8 ml |
| CaCl$_2$ | 0.17 ml |
| MgSO$_4$ | 0.4 ml |
| NaHCO$_3$ | 1.0 ml |
| Dextrose | 0.22 mg |

Adjusted final volume to 100 ml with distilled H$_2$O and pH 7.2 immediately prior to use.

E) Bluing Agent

Dissolved 20 gm MgSO$_4$ and 2 gm NaHCO$_3$ in 1000 ml H$_2$O.

F) Acid-Alcohol Solution

Added 1 ml of HCl to 1000 ml 70% isopropyl alcohol.

G) N-formyl-1-methionyl-1-leucyl-1-phenylalinine (f-met-leuphe) (Sigma Chemical)

The stock solution of $10^{-3}$M was prepared by dissolving 4.38 mg in 10 ml DMSO, and stored in −4° C., $1 \times 10^{-8}$M solution was prepared in HBSS.

H) Ficoll-Paque ® solution (Pharmacia)

Equipment

A) Optimax 40-10 Image Analyzer
B) Model T3-6 Centrifuge (Beckman)

Filters

Membranes, 5μM obtained from Millipore Corporation after pre-testing for lot variation.

Isolation of Cells

A) Equal parts of citrated peripheral venous blood drawn from a normal volunteer were mixed with saline containing 6% dextran. The mixture was allowed to sediment for 30-40 minutes in a 50 ml polypropylene centrifuge tube.

B) The plasma was decanted and centrifuged at 1500 rpm for 7 minutes and washed with saline.

C) The supernatant was decanted and the contaminating red blood cells were eliminated by adding ice cold lysing solution and allowing the cell suspension to stand on ice for 5 minutes.

D) The cells were washed and resuspended in saline and 7 ml of the cell suspension was carefully layered over 3 ml Ficoll-Paque in a 16×100 mm glass round bottom tube.

E) The tubes were centrifuged at 400g for 30 minutes at room temperature.

F) The supernatant was decanted and the PMNs (pelleted on the bottom of the tubes) were washed with saline and with Hanks buffer. The cells were adjusted to a final concentration of $3 \times 10^6$ cells/ml in Hanks buffer containing 0.5% BSA.

Chemotaxis Assay

A) Bottom Chamber:
1) Chemoattractant: serial dilution was prepared of the stocks ($10^{-3}$M) N-Formyl-methionyl-leucyl-phenylalanine in Hanks buffer and 130 μl of $1 \times 10^{-8}$M solution was pipetted into the lower bottom chamber. The bottom chamber of the negative control was filled with saline.

2) Placed Millipore membranes to completely cover the wells and allowed the liquid to absorb.

3) Placed on upper chamber and tighten retaining nuts.

B) Top Chamber:
1) Sample preparation: Mixed equal volume of sample diluted in Hanks buffer containing 0.5 ml BSA and cell suspension in a test tube prior to pipetting 200 μl into appropriate duplicate chambers.
2) Incubated chambers at 37° C. for 40-60 minutes.

C) Staining of Membranes:
1) The membranes were carefully placed in numbered staining racks and the cells were fixed in 100% isopropyl alcohol for 3 minutes.
2) Stained in hematoxylin Gill's formulation No. 1 for 6 minutes.
3) Rinsed in distilled water for 0.5 minutes
4) Rinsed in acid-alcohol mixture for 0.3 minutes.
5) Rinsed in distilled water for 0.5 minutes.
6) Rinsed in bluing agent for 5.0 minutes.
7) Rinsed in distilled water for 0.5 minutes.
8) Rinsed in 100% isopropyl alcohol in 1-2 minutes.
9) The filters were allowed to air dry thoroughly and mounted on microscope slides with coverslips using type B immersion oil.
10) Three to five fields per membrane were counted with the aid of the Image Analyser (optimal 40-10). Special effort was made to select a standard for evaluating the cell monolayer in which the distribution of cells in the field of view is uniform. The number of cells at each 20μM level beneath the selected monolayer was then counted and the chemotactic index (CI) calculated by multiplying the individual cell count at each level by their corresponding depth of penetration, and taking the sum of these numbers.
11) The results in Table II are recorded as percent inhibition. Percent inhibition by each thienylbenzylamime was calculated as follows:

$$\frac{CI \text{ at given concentration } - \text{ background}}{CI \text{ of the control } - \text{ background}} \times 100$$

The CI of the control was determined by conducting the assay with N-formyl-methionyl-leucylphenylalanine (FMLP) alone without any thienlbenzylamine. The background was determined by conducting the assay without any FMLP.

TABLE II

| EFFECT OF THIENYLBENZYLAMINES ON HUMAN PMN CHEMOTAXIS | | |
|---|---|---|
| | PERCENT INHIBITION | |
| COMPOUND | 0.01 μm | 1 μM |
| 21 | 35 | 54 |
| 22 | | 29 |
| 23 | | 34 |
| 24 | | 19 |
| 33 | 26 | 26 |
| 2 | 57 | 76 |
| 3 | 14 | 39 |
| 4 | 12 | 55 |
| 5 | 34 | 34 |
| 6 | 24 | 25 |
| 7 | 37 | 41 |
| 8 | 35 | 42 |
| 9 | 23 | 49 |
| 11 | 37 | 33 |
| 12 | 54 | 52 |
| 14 | 0 | 51 |

What is claimed is:
1. An antiinflammatory compound of the formula:

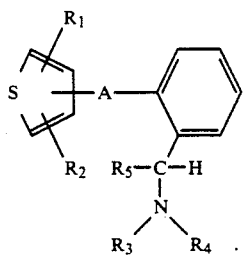

or

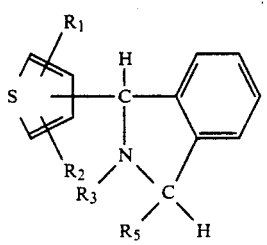

wherein
R₁ is hydrogen, phenyl, halogen, alkyl of from 1 to carbon atoms, dialkylaminoalkyl of from 3 to 5 carbon atoms, or acyl of from 3 to 5 carbon atoms;
R₂ is hydrogen, halogen or alkyl of 1 to 5 carbon atoms;
R₃ and R₄ are each hydrogen, alkyl of from 1 to 5 carbon atoms, or hydroxyalkyl of from 1 to 2 carbon atoms;
R₅ is hydrogen or alkyl of from 1 to 5 carbon atoms; and

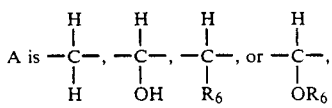

wherein
R₆ is alkyl of from 1 to 5 carbon atoms, or a physiologically acceptable salt of the compound.

2. An inflammatory compound as recited in claim 1 wherein the compound has the formula

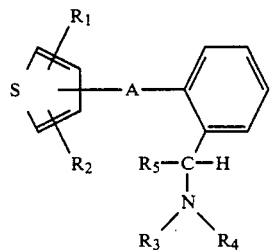

and A and R₁-R₅ are recited in claim 1.

3. An antiinflammatory compound as recited in claim 2 wherein
R₁ is hydrogen, halogen or methyl;
R₂ is hydrogen, halogen or methyl;
R₃ is hydrogen or methyl;
R₄ is hydrogen or methyl;
R₅ is hydrogen or methyl; and

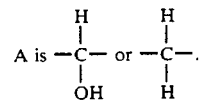

4. An antiinflammatory compound as recited in claim 3 wherein
R₁ is halogen;
R₂ is halogen;
R₃ is methyl;
R₄ is methyl;
R₅ is hydrogen or methyl; and

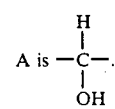

5. An antiinflammatory compound as recited in claim 1 wherein in the compound has the formula

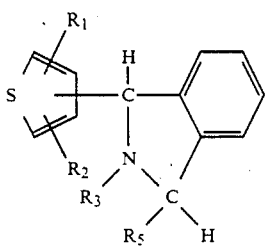

and R₁, R₂, R₃ and R₅ are recited in claim 1.

6. An antiinflammatory compound as recited in claim 5 wherein R₁ is hydrogen, halogen or methyl; R₂ is hydrogen, halogen or methyl; R₂ is hydrogen, halogen or methyl; R₃ is hydrogen or methyl; and R₅ is hydrogen or methyl.

7. An anti-inflammatory compound as recited in claim 5 wherein R₁ is halogen; R₂ is halogen; R₃ is methyl; and R₅ is hydrogen or methyl.

8. A method for treating inflammation in a patient requiring such treatment, which comprises administering to the patient a therapeutically effective amount of a compound of the formula

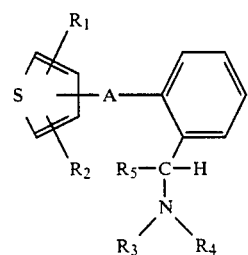

or

-continued

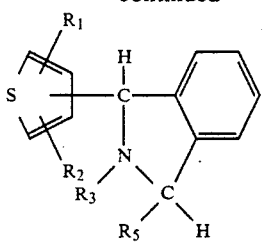
(II)

wherein $R_1$ is hydrogen, phenyl, halogen, alkyl of from 1 to 5 carbon atoms, dialkylaminoalkyl of from 3 to 5 carbon atoms, or acyl of from 3 to 5 carbon atoms;

$R_2$ is hydrogen, halogen or alkyl of from 1 to 5 carbon atoms;

$R_3$ and $R_4$ are each hydrogen, alkyl of from 1 to 5 carbon atoms or hydroxyalkyl of from 1 to 2 carbon atoms;

$R_5$ is hydrogen or alkyl of from 1 to 5 carbon atoms; and

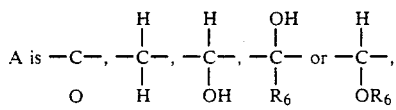

wherein $R_6$ is alkyl of from 1 to 5 carbon atoms, or a physiologically acceptable salt of the compound.

9. A method as recited in claim 7 wherein the compound has the formula

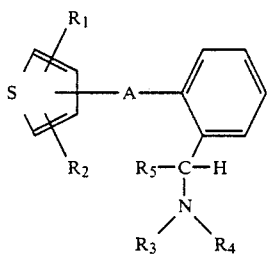
(I)

and A and $R_1$-$R_5$ are recited in claim 7.

10. A method as recited in claim 8 wherein $R_1$ and $R_2$ are each hydrogen, halogen or methyl; $R_3$, $R_4$ and $R_5$ are each hydrogen, or methyl; and A is

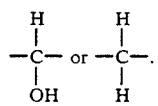

11. A method as recited in claim 9 wherein $R_1$ and $R_2$ are each halogen; $R_3$ and $R_4$ are each methyl; $R_5$ is hydrogen or methyl; and A is

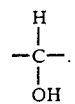

12. A method as recited in claim 7 wherein the compound has the formula

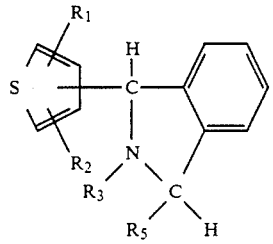
(II)

and $R_1$, $R_2$, $R_3$ and $R_5$ are as recited in claim 7.

13. A method as recited in claim 11 wherein $R_1$ and $R_2$ are each hydrogen, halogen or methyl; and $R_3$ and $R_5$ are each hydrogen or methyl.

14. A method as recited in claim 11 wherein $R_1$ and $R_2$ are each halogen; $R_3$ is methyl; and $R_5$ is hydrogen or methyl.

15. A pharmaceutical composition useful for the treatment of inflammation comprising a therapeutically effective amount of the compound recited in claim 1, and a physiologically acceptable carrier.

16. A pharmaceutical composition useful for the treatment of inflammation comprising a therapeutically effective amount of the compound recited in claim 2, and a physiologically acceptable carrier.

17. A pharmaceutical composition useful for the treatment of inflammation comprising a therapeutically effective amount of the compound recited in claim 3, and a physiologically acceptable carrier.

18. A pharmaceutical composition useful for the treatment of inflammation comprising a therapeutically effective amount of the compound recited in claim 4, and a physiologically acceptable carrier.

19. A pharmaceutical composition useful for the treatment of inflammation comprising a therapeutically effective amount of the compound recited in claim 5, and a physiologically acceptable carrier.

20. A pharmaceutical composition useful for the treatment of inflammation comprising a therapeutically effective amount of the compound recited in claim 6, and a physiologically acceptable carrier.

21. A pharmaceutical composition useful for the treatment of inflammation comprising a therapeutically effective amount of the compound recited in claim 7, and a physiologically acceptable carrier.

* * * * *